United States Patent
Levin et al.

(10) Patent No.: US 10,028,814 B2
(45) Date of Patent: Jul. 24, 2018

(54) X-SHAPED DEVICE AND METHOD FOR DEPLOYMENT AND PLACEMENT OF A PATCH

(75) Inventors: Ofek Levin, Moshav Amirim (IL); Arie Levy, Ramat-Gan (IL)

(73) Assignee: Covidien LP, Mansfield, MA (US)

( * ) Notice: Subject to any disclaimer, the term of this patent is extended or adjusted under 35 U.S.C. 154(b) by 1092 days.

(21) Appl. No.: 13/576,491

(22) PCT Filed: Feb. 1, 2011

(86) PCT No.: PCT/IB2011/000301
§ 371 (c)(1),
(2), (4) Date: Jan. 9, 2014

(87) PCT Pub. No.: WO2011/095890
PCT Pub. Date: Aug. 11, 2011

(65) Prior Publication Data
US 2014/0114331 A1    Apr. 24, 2014

(51) Int. Cl.
A61B 17/08    (2006.01)
A61F 2/00    (2006.01)
A61B 17/02    (2006.01)

(52) U.S. Cl.
CPC .......... *A61F 2/0063* (2013.01); *A61F 2/0095* (2013.01); *A61B 17/0218* (2013.01); *A61F 2002/0072* (2013.01)

(58) Field of Classification Search
CPC ...... A61B 17/0218; A61B 2017/00623; A61B 17/28; A61B 17/30; A61B 17/02; A61F 2002/0072; A61F 2/0063; A61F 2/0095

USPC ........... 623/23.72, 23.74; 606/151, 213, 198
See application file for complete search history.

(56) References Cited

U.S. PATENT DOCUMENTS

| | | |
|---|---|---|
| 5,122,155 A | 6/1992 | Eberbach |
| 5,258,000 A | 11/1993 | Gianturco |
| 5,263,969 A | 11/1993 | Phillips |
| 5,304,187 A | 4/1994 | Green et al. |
| 5,333,624 A | 8/1994 | Tovey |
| 5,366,460 A | 11/1994 | Eberbach |
| 5,370,650 A | 12/1994 | Tovey et al. |
| 5,383,477 A | 1/1995 | DeMatteis |
| 5,397,331 A | 3/1995 | Himpens et al. |

(Continued)

FOREIGN PATENT DOCUMENTS

| | | |
|---|---|---|
| EP | 0706778 A1 | 4/1996 |
| FR | 2789888 A1 | 2/1999 |

(Continued)

OTHER PUBLICATIONS

US 5,318,559, 04/1994, Green et al. (withdrawn)

(Continued)

*Primary Examiner* — Diane Yabut
*Assistant Examiner* — Erich Herbermann

(57) ABSTRACT

This invention generally relates to a device and method for repairing biological tissue aperture. In certain embodiments, the invention provides a system for closing an aperture in a biological tissue that includes a handle, a shaft connected to the handle, and a deployment scaffold connected to the shaft, in which the scaffold is configured to releasably retain a surgical implant and the scaffold includes an open configuration and a closed configuration, the open configuration being substantially X-shaped.

22 Claims, 8 Drawing Sheets

(56) References Cited

U.S. PATENT DOCUMENTS

| | | | |
|---|---|---|---|
| 5,405,360 A * | 4/1995 | Tovey | 606/151 |
| 5,464,403 A | 11/1995 | Kieturakis et al. | |
| 5,713,948 A * | 2/1998 | Uflacker | A61F 2/07 606/194 |
| 6,478,803 B1 | 11/2002 | Kapec et al. | |
| 6,575,988 B2 | 6/2003 | Rousseau | |
| 6,582,451 B1 * | 6/2003 | Marucci | A61B 17/29 606/207 |
| 6,730,119 B1 * | 5/2004 | Smalling | A61F 2/07 606/194 |
| 7,591,813 B2 * | 9/2009 | Levine et al. | 604/528 |
| 2003/0135257 A1 * | 7/2003 | Taheri | A61B 17/00234 623/1.11 |
| 2004/0087980 A1 | 5/2004 | Ford et al. | |
| 2004/0117032 A1 * | 6/2004 | Roth | 623/23.72 |
| 2005/0131520 A1 * | 6/2005 | Zilla | A61F 2/06 623/1.13 |
| 2006/0189918 A1 | 8/2006 | Barker | |
| 2007/0185506 A1 | 8/2007 | Jackson | |
| 2007/0203507 A1 | 8/2007 | McLaughlin et al. | |
| 2008/0188874 A1 | 8/2008 | Henderson | |
| 2008/0195121 A1 | 8/2008 | Elder et al. | |
| 2009/0248092 A1 | 10/2009 | Belles et al. | |
| 2010/0234938 A1 * | 9/2010 | Taheri | A61B 17/22031 623/1.23 |
| 2010/0312357 A1 | 12/2010 | Levin et al. | |
| 2011/0230947 A1 * | 9/2011 | Hartley | A61F 2/95 623/1.11 |

FOREIGN PATENT DOCUMENTS

| | | |
|---|---|---|
| WO | WO 2004/080348 A1 | 9/2004 |
| WO | WO 2008/045635 A2 | 4/2008 |
| WO | 2009104182 A2 | 8/2009 |
| WO | 2010046893 A1 | 4/2010 |

OTHER PUBLICATIONS

International Search Report of International Application No. PCT/IB 11/00301, dated Jul. 15, 2011 (1 page).
European Search Report EP 11 73 9467 dated Feb. 18, 2015.

* cited by examiner

X-SHAPED DEVICE AND METHOD FOR DEPLOYMENT AND PLACEMENT OF A PATCH

RELATED APPLICATION

This application is a National Stage Application of PCT/US2011/023312 filed Feb. 1, 2011 under 35USC § 371 (a), which claims benefit of and priority to U.S. Provisional Patent Application Ser. No. 61/300,839 filed Feb. 3, 2010, the contents of which are incorporated by reference herein in its entirety.

FIELD OF THE INVENTION

This invention generally relates to a device and method for repairing biological tissue aperture. More specifically, the present invention relates to a device and method for deploying patch to a biological tissue during surgery.

BACKGROUND OF THE INVENTION

An object of the present invention is to provide apparatus and a method for performing corrective surgery on internal wounds such as hernia where invasion of the patient's body tissues is minimized and the resultant trauma is reduced.

A hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first deploy the patch and then attach the patch to the tissue.

There are a few patent and patent applications teaching the deployment of patches. For example U.S. Pat. No. 5,836,961 (refers hereinafter as '961) which relates to an apparatus used for developing an anatomic space for laparoscopic hernia repair and a patch for use therewith. The apparatus of patent '961 comprises a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. The apparatus comprises an inflatable balloon. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

Although patent '961 relates to deploying means, patent '961 teaches a device in which the patch is attached to a balloon which is introduced into the abdominal cavity; patent '961 does not disclose means for enabling flexibility of the system to better fit itself to the landscape of the tissue. In other words, there is no disclosure of means of articulating so as to provide better compatibility of the deployment system and the tissue.

Another example for deploying the patch can be found in U.S. Pat. No. 5,370,650 (refers hereinafter as '650) which relates to an apparatus for positioning surgical implants adjacent to body tissue to facilitate the fastening of the implant to the body tissue. Patent '650 provides an apparatus for positioning surgical implants adjacent to body tissue, comprising an outer tube having a proximal end, a distal end and a longitudinal axis; an inner rod at least partially disposed within the outer tube and slidable along said longitudinal axis. The inner rod has a proximal and a distal end portions.

The inner rod distal end portion further comprises articulating means for pivoting at an angle with respect to the longitudinal axis (a preferred embodiment illustrating the teaching of patent '650 is illustrated in FIG. 11). The articulation is provided by a spring-like flexible rod 18 encapsulated within rigid tube 12. By pulling tube 12, the flexible rod 18 bends and hence provide articulation.

More patent literature can be found in PCT no. WO08065653 (refers hereinafter as '653) relates to a device especially adapted to deploy a patch within a body cavity. The device is an elongate open-bored applicator (EOBP) and comprises (a) at least one inflatable contour-balloon, (b) at least one inflatable dissection balloon. The inflatable contour-balloon and the inflatable dissection balloon are adjustable and located at the distal portion. The EOBP additionally comprises (c) at least one actuating means located at the proximal portion. The actuating means is in communication with the inflatable contour-balloon and the inflatable dissection balloon. The actuating means is adapted to provide the inflatable contour-balloon and the inflatable dissection balloon with independent activation and/or de-activation.

It should be pointed out that PCT '653 does not disclose nor claim articulation means.

Articulation is highly important since it enables the optimum positioning and orientation of the patch relatively to the hernia. Such optimum positioning and orientation is provided no matter what is the entrance angle of the patch to the abdominal cavity.

None of the patent literatures found to teach articulating means for providing optimal positioning and orientation of the patch relatively to the tissue.

Hence there is still a long felt need for a patch deployment mechanism enabling such articulation.

SUMMARY OF THE INVENTION

It is one object of the present invention to provide an x-shaped, lateral patch deployment device comprising
  a. at least two deployment arms (DAs) 108 centrally coupled together to form said x-shaped device; said DAs are characterized by at least two configurations (i) a parallel configuration in which said two DAs are substantially parallel to each other; and, (ii) a perpendicular configuration, in which said two DAs are substantially perpendicular to each other; said DAs are adapted to be reversibly transformed from said parallel configuration to said perpendicular configuration;
  b. at least two frame arms (FA) 104, adapted to be reversibly coupled to said patch; each of which is coupled to the distal portion of one of said DA 108 via a slidable track 112; such that when said DAs 108 are in said parallel configuration, said FAs are substantially adjacently positioned; and when said DAs are in said perpendicular configuration, said FAs are substantially apart so as to provide said patch deployment.

It is another object of the present invention to provide the device as defined above, additionally comprising at least two deployment wires (DW) 114 coupled to the distal end of each of said DAs, adapted to reversibly transform said DA from said parallel configuration to said perpendicular configuration.

It is another object of the present invention to provide the device as defined above, wherein said DW 114 additionally utilized for lateral rotation of said distal portion.

It is another object of the present invention to provide the device as defined above, additionally comprising at least one deployment rod 117 coupled to at least one of said DAs 108, adapted to reversibly transform said DAs from said parallel configuration to said perpendicular configuration.

It is another object of the present invention to provide the device as defined above, additionally comprising a central shaft 105 and at least one deployment rod 117; said central shaft is adapted to reciprocally move along the main longitude axis of said device; said deployment rod 117 is hinge-like coupled to the distal end of said central shaft 105 and to the distal portion of at least one of said DAs 108; wherein said transformation of said DAs from said parallel configuration to said perpendicular configuration and back is obtained by said reciprocal movement of said central shaft 105.

It is another object of the present invention to provide a zigzag-shaped lateral patch deployment device comprising
  a. at least two pairs of deployment arms (DAs) 108, each of which is centrally coupled together to form an x-shaped mechanism; each of said pair of DAs are characterized by at least two configurations (i) a parallel configuration in which said pair of DAs are substantially parallel to each other; and, (ii) a perpendicular configuration, in which said pair of DAs are substantially perpendicular to each other; each pair of DAs is coupled together to form said zigzag shaped device; the center of said zigzag shaped device is coupled to a central shaft 105; such that a reciprocal movement of said central shaft 105 reversibly transform said DAs from said parallel configuration to said perpendicular configuration;
  b. at least two frame arms (FA) 104, adapted to be reversibly coupled to said patch; each of which is coupled to the distal portion of one of said DA 108 via a slidable track 112; such that when said DAs are in said parallel configuration, said FAs are substantially adjacently positioned; and when said DAs are in said perpendicular configuration, said FAs are substantially apart so as to provide said patch deployment.

It is another object of the present invention to provide a method of deploying a hernia patch. The method comprising steps selected from:
  a. obtaining an x-shaped, lateral patch deployment device comprising:
    i. at least two deployment arms (DAs) 108 centrally coupled together to form said x-shaped device; said DAs are characterized by at least two configurations (i) a parallel configuration; and, (ii) a perpendicular configuration;
    ii. at least two frame arms (FA) 104, adapted to be reversibly coupled to said patch;
  b. providing said Das in said parallel configuration;
  c. coupling each of said FA to the distal portion of one of said DA 108 via a slidable track 112;
  d. transforming said DAs 108 from said parallel configuration to said perpendicular configuration such that said FAs are substantially apart from each other; thereby deploying said patch.

It is another object of the present invention to provide the method as defined above, additionally comprising step of providing said x-shaped, lateral patch deployment device with at least two deployment wires (DW) 114 coupled to the distal end of each of said DAs, adapted to reversibly transform said DA from said parallel configuration to said perpendicular configuration.

It is another object of the present invention to provide the method as defined above, additionally comprising step of utilizing said DW 114 for lateral rotation of said distal portion.

It is another object of the present invention to provide the method as defined above, additionally comprising step of providing said x-shaped, lateral patch deployment device with at least one deployment rod 117 coupled to at least one of said DAs 108, adapted to reversibly transform said DAs from said parallel configuration to said perpendicular configuration.

It is lastly an object of the present invention to provide a method of deploying a hernia patch. The method comprising steps selected from:
  a. obtaining a zigzag-shaped lateral patch deployment device comprising:
    i. at least two pairs of deployment arms (DAs) 108, each of which is centrally coupled together to form an x-shaped mechanism; each of said pair of DAs are characterized by at least two configurations (i) a parallel configuration; and, (ii) a perpendicular configuration; each pair of DAs is coupled together to form said zigzag shaped device;
    ii. at least two frame arms (FA) 104, adapted to be reversibly coupled to said patch;
  b. coupling the center of said zigzag shaped device to a central shaft 105;
  c. providing said Das in said parallel configuration;
  d. coupling each of said FA to the distal portion of one of said DA 108 via a slidable track 112; and, e. reciprocally moving said central shaft 105 thereby transforming said DAs 108 from said parallel configuration to said perpendicular configuration such that said FAs are substantially apart from each other; thereby deploying said patch.

DETAIL DESCRIPTION OF THE SPECIFIC EMBODIMENTS

Figure 1A:
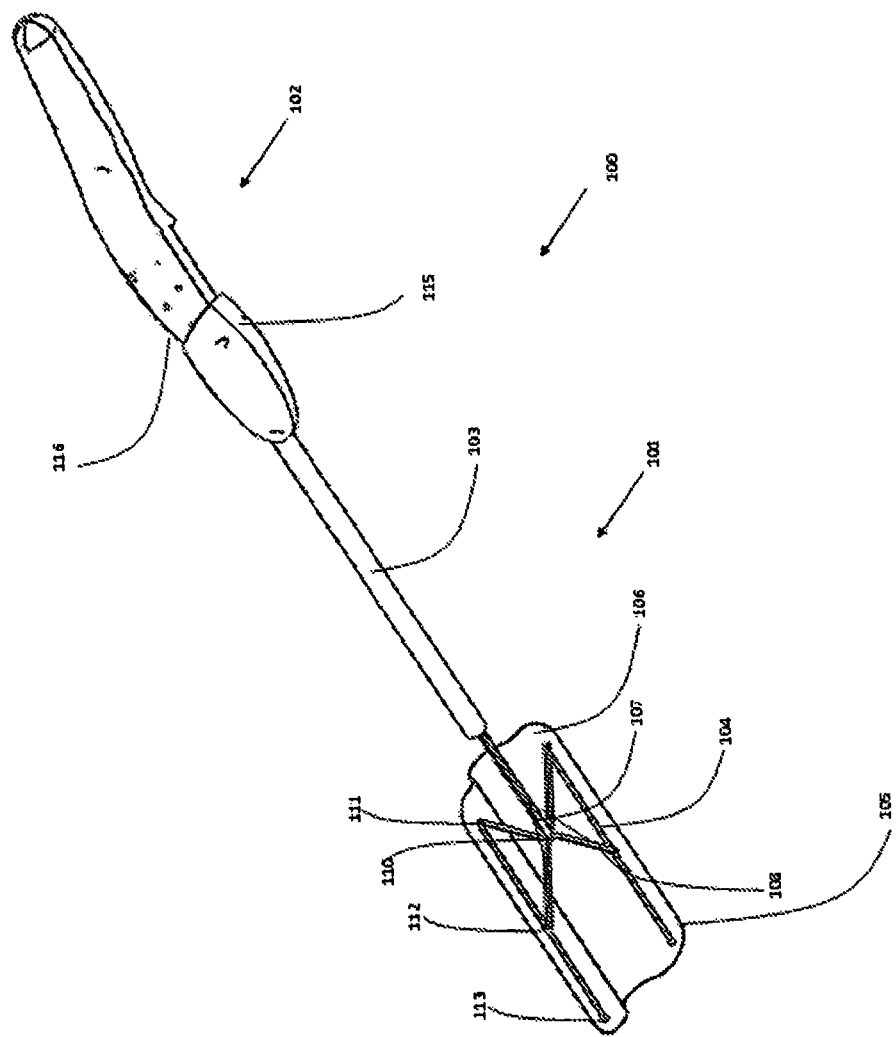
FIGS. 1A-1B illustrate one embodiment of the present invention.

The following description is provided, alongside all chapters of the present invention, so as to enable any person skilled in the art to make use of the invention and sets forth the best modes contemplated by the inventor of carrying out this invention. Various modifications of the present disclosure should be apparent to those skilled in the art, since the generic principles of the present invention have been defined specifically to provide a device and method for deploying a patch and optimally positioning said patch with respect to the hernia.

The present invention provides an x-shaped lateral deployment device (x-LDD) wherein the x-LDD is adapted to actively deploy and place a prostatic patch during surgery in order to allow proper location and orientation of the patch with respect to the treated tissue defect. The present invention also provides a method for deploying and attaching a patch to a biological tissue during surgery utilizing the x-LDD device.

It should be emphasized that some of the major advantages of the present invention, with respect to the prior art, is to provide a deployment system or a deployment and attachment system that enables (a) an actively deployment—the deployment is actively controlled by the surgeon (as opposed to passive deployment); and (b) the deployment is lateral in respect to the entrance port, such that minimal amount of manipulation is needed in order to bring the patch its optimal position.

The term "Hernia" refers hereinafter to umbilical hernia, hiatal hernia, ventral hernia, postoperative hernia, epigastric hernia, spiegelian hernia, inguinal hernia and femoral hernia, generally any abdominal wall related hernia.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components. The term "hinge like connection" can refer to a standard hinge or to a living hinge (i.e., a thin flexible hinge (flexure bearing) made from plastic that joins two rigid parts together while allowing them to bend along the line of the hinge).

The term "controlled deployment" refers hereinafter to an implant deployment which is continuous. Thus, deployment using the presently disclosed implant deployment device is variable amongst a number of deployment levels between a fully opened position and a fully closed position rather than a binary arrangement that does not include any intermediate positions or levels between fully opened and fully closed. This is in contrast to some conventional deployment systems in which the deployment of the implant relies upon the elasticity of a loop member surrounding the implant such that the implant can be either fully folded or fully unfolded. No intermediate stages are enabled. In the present invention, there can be several deployment stages.

The term 'bidirectional' or 'fully reversible deployment' refers hereinafter to the deployment of the patch, which according to the present invention, is fully reversible. In other words, the patch deployment is bidirectional, i.e., the patch can be fully folded (i.e., deployed within the body) and then, if the surgeon desires, the patch can be fully unfolded simply by the reconfiguration of the flexible arms from the initial stage to the final stage and vice versa.

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "articulation" refers hereinafter to a joint or juncture between two segments of the device. The articulating means of the present invention provides the ability to better adjust the device to the curvature of the treated tissue.

The term "orientation" refers hereinafter to the rotation of the mesh/patch within the abdominal cavity so as to fit to the hernia. Usually the mesh/patch is elongated (e.g., rectangular or i.e., elliptical)—therefore it has different directions. By rotating the mesh within the abdominal cavity—one can decide which direction is turned where.

The term "adjusting" refers hereinafter to rolling, folding and winding of the patch, thus preparing and enabling the insertion of said patch into the abdominal cavity.

The term "lateral deployment" refers to a patch deployment in which the deployment mechanism is deployed laterally with respect to the trocar; such that once the patch is deployed, the plane of said patch is substantially parallel to said trocar.

The term "perpendicular deployment" refers to in which the deployment mechanism is deployed perpendicularly (or substantially not laterally) with respect to the trocar; such that once the patch is deployed, the plane of said patch is substantially perpendicular to said trocar.

Before explaining the figures, it should be understood that the invention is not limited in its application to the details of construction and the arrangement of the components set forth in the following description or illustrated in the drawings. The invention can be carried out in various ways.

Figure 1B:
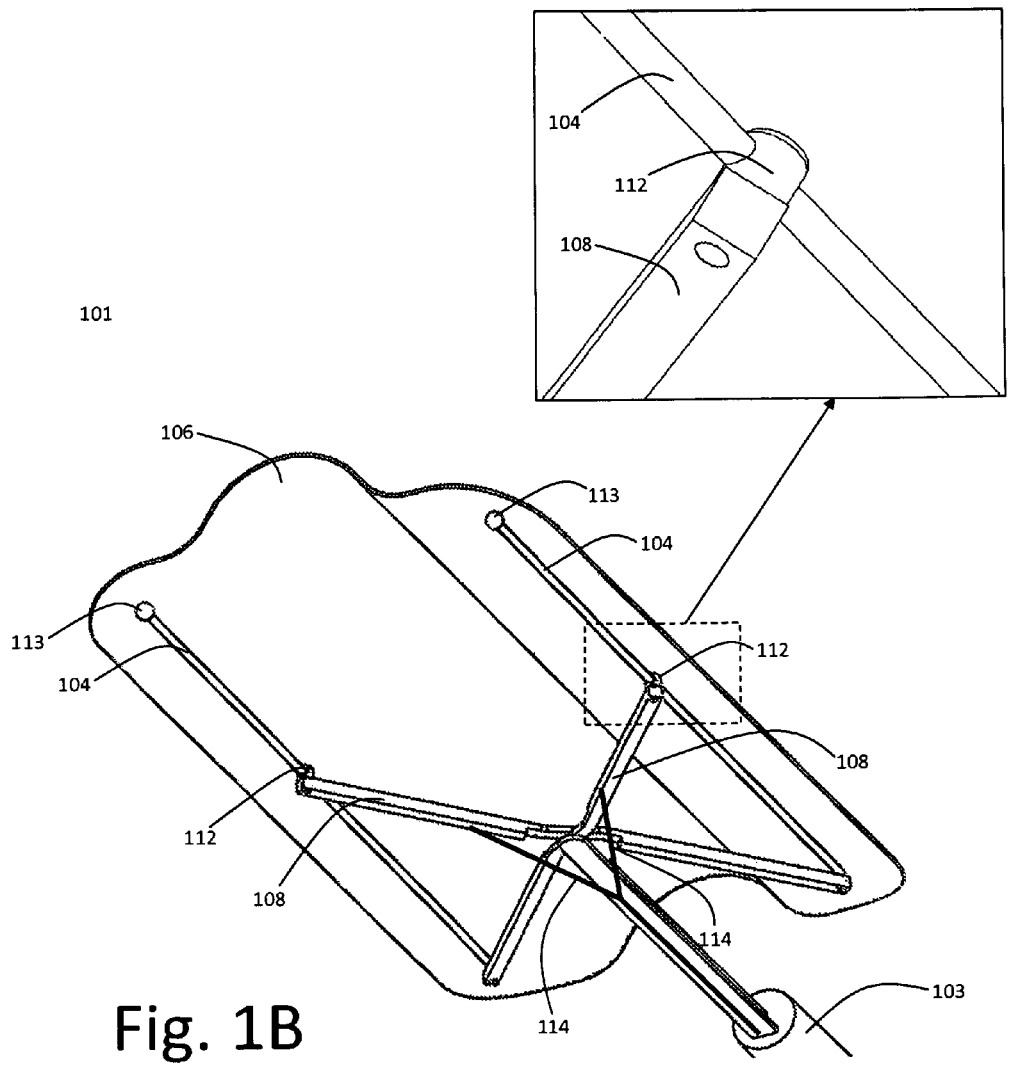

Reference is now made to FIGS. 1A-1B illustrating one embodiment of the present invention. According to that embodiment an x-shaped lateral deployment device (x-LDD) which is adapted for deployment and placement of a prosthetic patch during a minimal invasive (i.e., Laparoscopic) hernia repair surgery is provided.

The x-LDD 100 comprises of 2 main portions: distal portion 101, and a proximal portion 102. The two portions are connected via a tube 103. The distal portion is adapted to be inserted into a body during the surgery via a trocar. The distal portion is also adapted to deploy and place a prosthetic hernia repair patch 106 onto the patient's tissue surface.

The distal portion comprises of at least two frame arms (FA) 104, at least two deployment arms (DA) 108. said two DA 108 are coupled together to form said x-shaped deployment device.

According to the embodiment illustrated in FIGS. 1A-1B, each DA 108 is connected at its center to the distal end of tube 103 via a hinge 110 and a spring 115 (not shown at the drawing).

Spring 115 is needed in order to keep the system under tension—i.e., to enable a default configuration in which the x-LDD is closed.

Each FA 104 is connected at its proximal end to the proximal end of at least one of the DA 108 via a hinge 111. At least two slidable tracks 112 are provided. Each of which is adapted to slide on one FA. Each slidable track 112 is connected to the distal end of the second DA 108 (i.e., to the DA 108 which the FA 104 is not connected to) via a hinge. Track 112 enables the distal end of each DA 108 to slide along said FA 104.

According to one embodiment, a protection cap 113 is located at the distal end of each FA 104, adapted to prevent tissue damage that may be induced by the distal end of said FA 104.

According to one embodiment, each FA 104 is flexible such that it can substantially conforms to the patient's tissue once it is forced against it, therefore allowing patch 106 to be brought into sufficient contact with said patient's tissue.

Each of said DAs 108 is characterized by a plurality of configurations. One of said configuration is a parallel configuration in which the DAs are substantially parallel to said tube 103; another one of said configuration is a substantially perpendicular configuration in which said DAs are substantially perpendicular to said tube 103.

At the rest of said configurations, the DAs are positioned at an angle A with respect to said tube 103. Angle A can be at a range of about 0 degrees to about 180 degrees. Two deployment wires (DW) 114 are connected to the distal portion of each DA 108. DW 114 is adapted to pull each of said DA 108 such that it can be transformed form said parallel configuration into said perpendicular configuration. When no load is applied to DW 114, spring 115 holds DA 108 at its parallel configuration The patch/mesh/net 106 is reversibly attached to the FAs 104 by a patch attachment means (PAM) 107 (not shown in the figure).

Figure 1C:
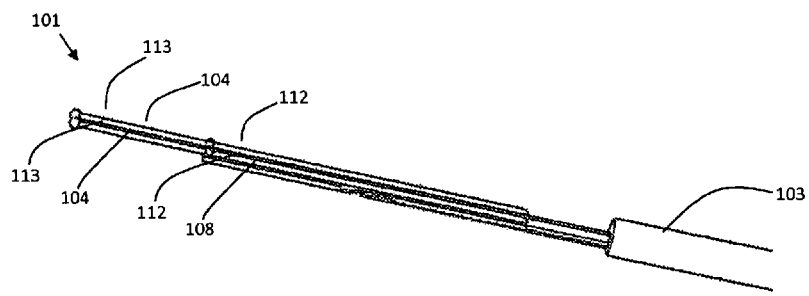
FIGS. 1C-1E illustrate the deployment mechanism of device as provided by the present invention.
Figure 1D:
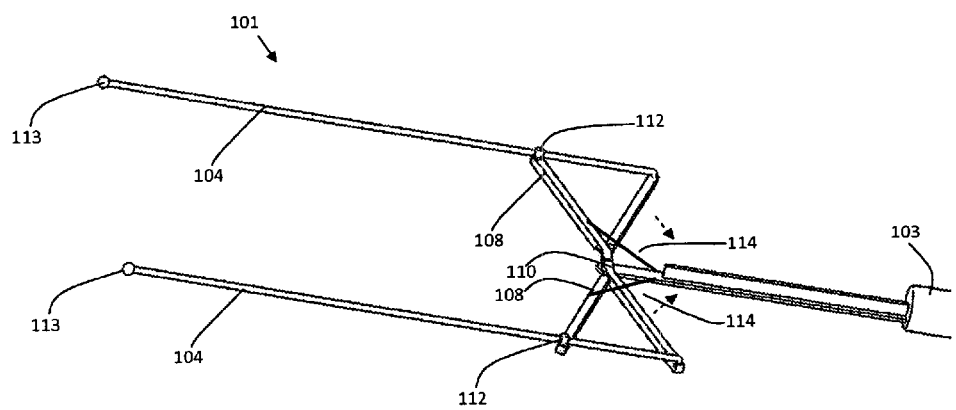
Figure 1E:
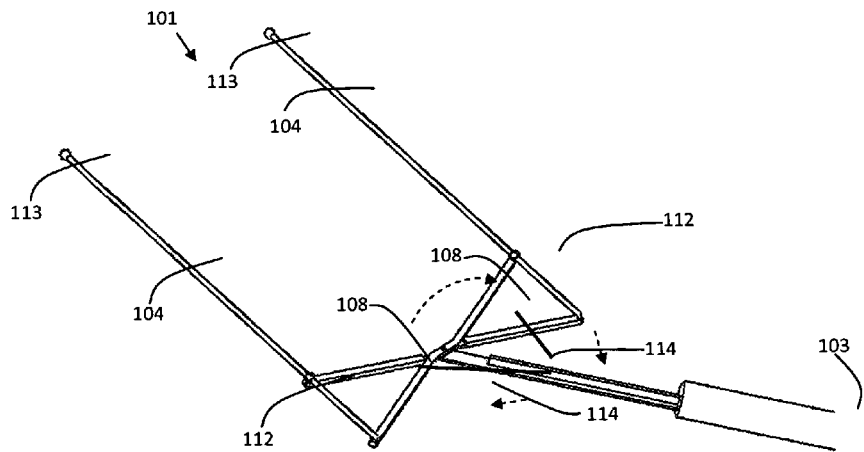

Reference is now made to FIGS. 1C-1E which illustrates the deployment mechanism of device 100. The close configuration is described in FIG. 1C while the deployed configuration is described in FIG. 1D.

Said closed configuration is obtained once the two DA 108 is in their parallel configuration such that the two FA 104 are substantially adjacent to one another (see FIG. 1C). When the system is in its closed configuration, the distal portion cross section area is less than the inner cross section area of the trocar such that patch 106 can be rolled onto the distal portion and inserted into the patient's abdominal cavity via said trocar.

As can be seen in FIG. 1D, once the device is inserted to the patient's abdominal cavity, patch 106 is deployed by pulling each DW 114 and transforming each DA 108 form its parallel configuration into its perpendicular configuration. As a result each FA 104 moves laterally away from tube 103, therefore deploying patch 106. The deployment process is controlled by a deployment lever 115 which is located in the handle, positioned in at the proximal portion 102.

Once the device is transformed into its deployed configuration, the two DA 108 are in contact with each other and cannot be further deployed; therefore, once the device is in its deployed configuration, lateral articulation of the entire distal portion 101 around hinge 110 can be obtained by pulling one of DW 114 while releasing the other (see FIG. 1E). Said lateral articulation is controlled by articulation lever 118 which is located in the handle, positioned in the proximal portion 102. Said articulation can be performed to either side of said tube 103.

Figure 1F:
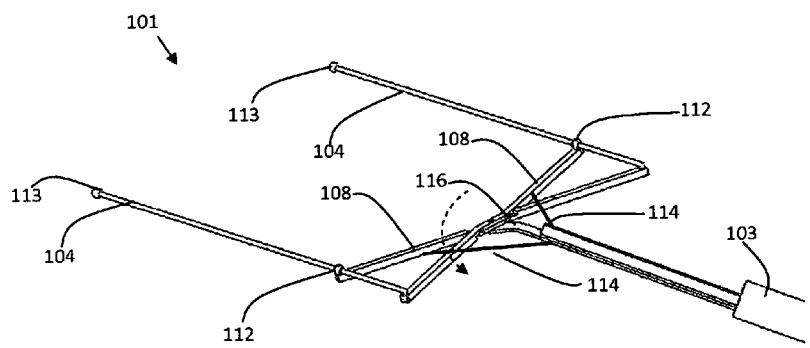
FIG. 1F illustrates one embodiment of the vertical articulation feature of the present invention.

Reference is now being made to FIG. 1F which descries one embodiment of the vertical articulation feature of the present invention. According to this embodiment, the device 100 comprises a vertical articulation section (VAS) 116 at the distal portion of tube 103. said VAS 116 is flexible such that entire distal portion 101 can be tilted with respect to tube 103 once said distal portion is forced against the patient tissue; this property allows the surgeon to substantially bring said patch 106 into contact with said patient's tissue.

Figure 2A:
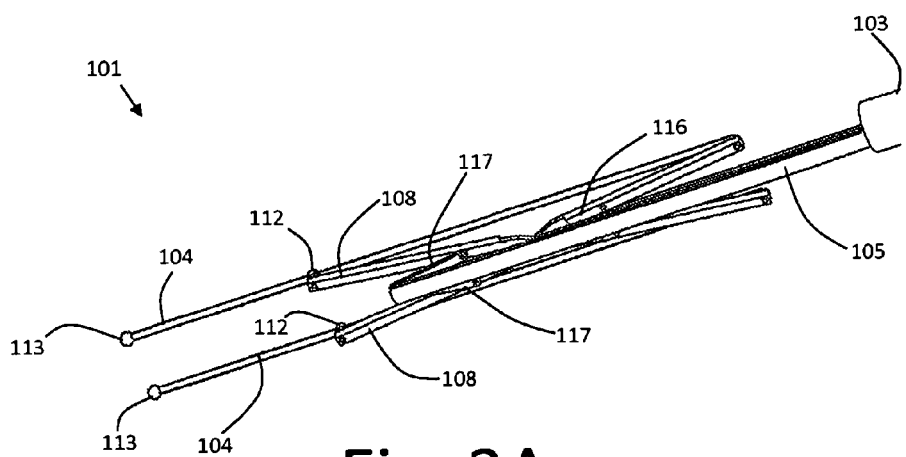
FIGS. 2A-2B illustrate another embodiment of the present invention.
Figure 2B:
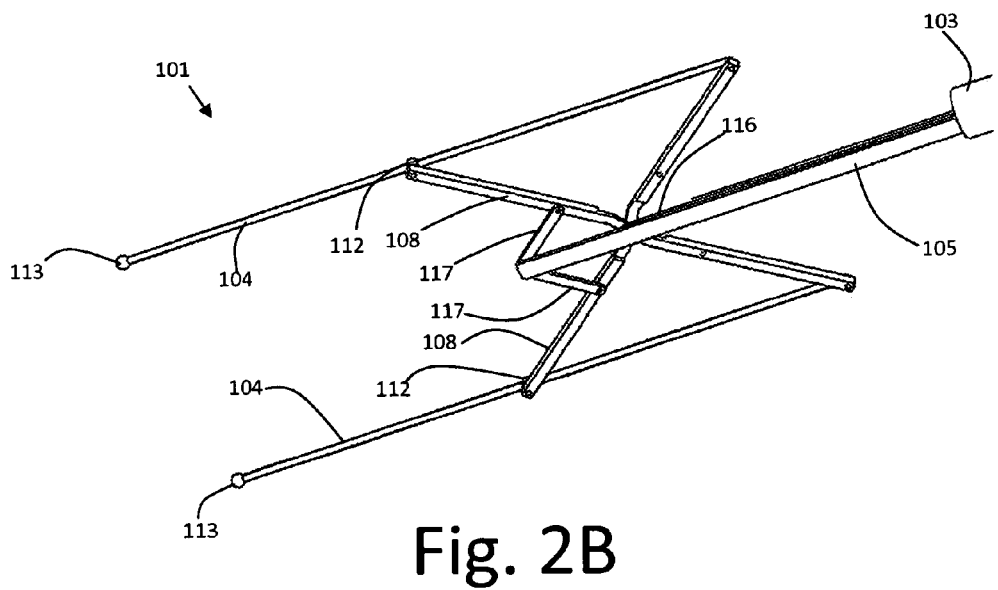

Reference is now being made to FIGS. 2A-2B which describes another embodiment of the present invention. According to this embodiment said device 100 comprises a central shaft 105 adapted to reciprocally move within tube 103 and at least two deployment rods 117. Each of said deployment rods 117 is connected to the distal end of said central shaft 105 and to distal portion of each of said DA 108.

Both connections are obtained by a hinge. According to this embodiment said transformation of the distal portion from its closed configuration into its deployed configuration is obtained by a reciprocal movement of said central shaft 105.

Said deployment rods 117 are characterized by at least two configurations: (i) a parallel configuration, in which said deployment rods 117 are substantially parallel to said central shaft 105 (and hence said DA 108 are in their parallel configuration and said device is closed); and, (ii) a perpendicular configuration, in which said deployment rods 117 are substantially perpendicular to said central shaft 105 (and hence said DA 108 are in their perpendicular configuration and said device is deployed).

Reference is now being made to FIGS. 3A-3D which describes yet another embodiment of the present invention. According to this embodiment, device 100 comprises two sets of DAs 108. Each set comprises a distal DA 108*a* and a proximal DA 108*b*. Each said distal DA 108*a* and proximal DA 108*b* are connected together via a hinge 301.

Each DA 108*a* is connected to the distal end of tube 103 at its proximal, and to the FA 104 at its distal portion via slidable track 112, both said connection are made via a hinge. Each DA 108*b* is connected to the distal portion of said central shaft 105 at its distal end via a hinge. The proximal end of each DA 108*b* in connected to the FA 104 via a hinge (see FIG. 3D).

Figure 3A:
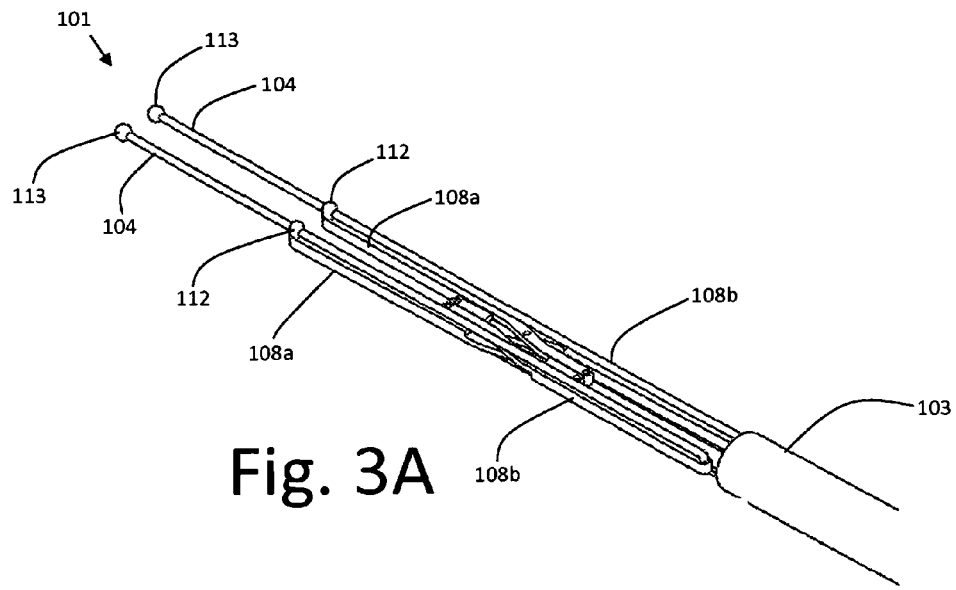
FIGS. 3A-3D illustrate yet another embodiment of the present invention.
Figure 3B:
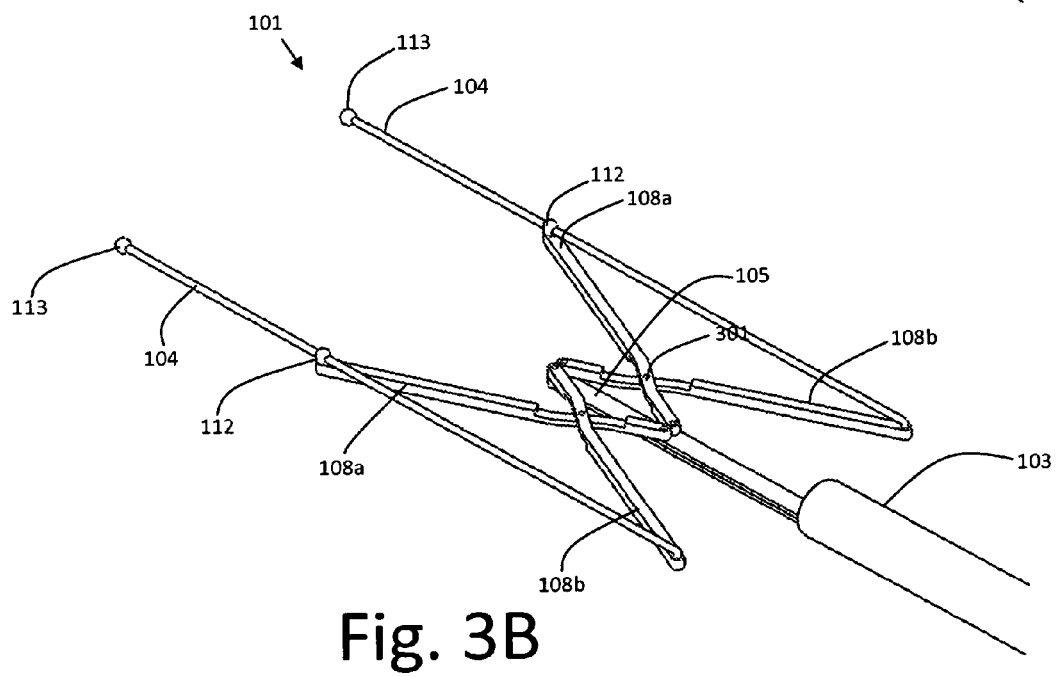
Figure 3C:
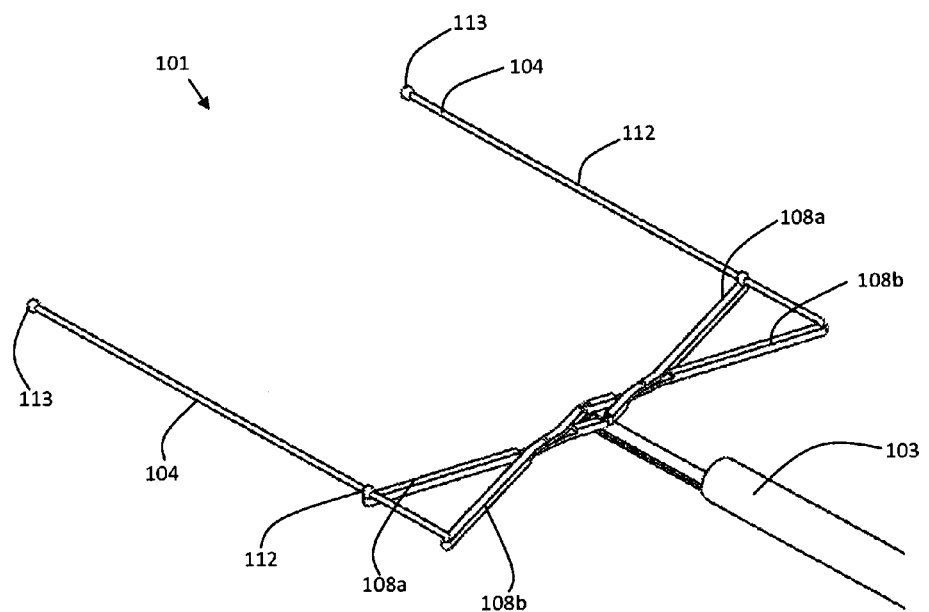
Figure 3D:
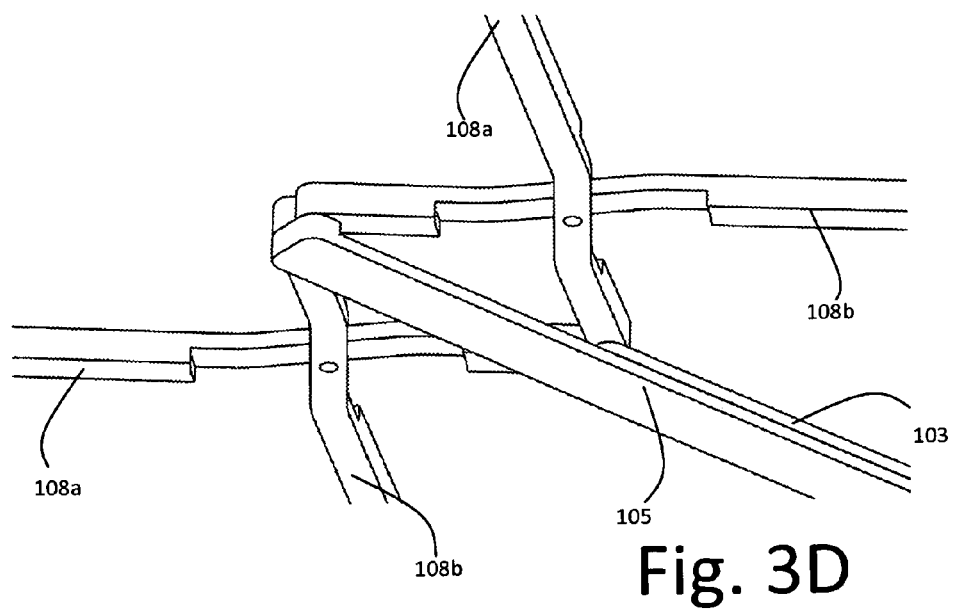

By reciprocally moving central shaft 105 towards the proximal portion 102 the connection between the two DA 108*b* and said central shaft 105 moves towards the proximal portion 102 and transform the device to its deployed configuration (see FIG. 3C).

Similarly, by reciprocally moving central shaft 105 towards the distal portion 101 the connection between the two DA 108*b* and said central shaft 105 moves towards the distal portion 101 and transform the device to its closed configuration.

As described above, the present invention also provides a method of utilizing the x-LDD 100 (as described above) during a laparoscopic hernia repair surgery. The method comprises steps selected inter alia from:

1. Obtaining a prosthetic patch 106, and an x-LDD 100 in its open state.
2. Attaching patch 106 to the distal portion 101 of the x-LDD 100.
3. Transforming the x-LDD 100 from its open configuration (deployed configuration) to its closed configuration using the deployment lever 113.
4. Rolling the patch 106 onto the distal portion 101.
5. Inserting the distal portion 101 together with the rolled patch 106 into the patient's abdominal cavity 401 trough the trocar 114.
6. Unrolling the patch 106 by slightly shaking the distal portion 101 or via a grasper.
7. Spreading (deploying) patch 106 by transforming the distal portion 101 from its closed configuration to its open configuration using the deployment lever 113.
8. Laterally rotating the distal portion 101 and hence patch 106, until it reaches the proper orientation of the patch with regards to the hernia defect.
9. Elevating the distal portion to proximate the hernia defect, and verifying correct location of the patch 106 with regards to the hernia defect.
10. Correcting the location and/or the orientation of the patch, if necessary.
11. Pressing the distal portion 101 and the patch 106 against the patient's tissue 204 near the hernia defect until the distal portion 101 is proximally aligned with the patient's tissue around the hernia defect.
12. Attaching the patch 106 to the patient's tissue 204 using attachment mean—e.g., hernia tacks, sutures.
13. Disengaging the distal portion 101 from the patch 106 and removing the distal portion 101 away from the patch 106.
14. Rotating back the distal portion 101 into its initial straight lateral angle using the articulation lever 112.
15. Transforming the distal portion 101 from its deployed configuration to its closed configuration.
16. Extracting the distal portion out of the patient's abdominal cavity.

Said patch location verification describe in step 9 can be performed by a number of different mechanisms:
(a) If the patch 106 is transparent enough to observe the hernia defect trough it, the patch 106 can be move to its desired location while it is close to or slightly pressed against the tissue, prior to attachment between the patch 106 and the patient's tissue. The surgeon, using the laparoscopic camera, can verify that there are sufficient margins between the hernia defect edges and the patch 106 edges.
(b) If the patch 106 is not transparent enough to enable observation of the hernia defect through it, the patch 106 location can be verified by bridging it approximately to the optimal location, and then lowering it a few centimeters down to a point in which the hernia defect can be viewed together with the patch 106. Then, the location can be adjusted. Once the patch is in its correct location it can be raised and presses to the tissue.
(c) Yet another method to verify the location of patch 106 is to first mark the center of the patch 106 and the center of the hernia at the patient's skin surface, prior to patch insertion. Once the mesh is inserted and deployed, a long needle is inserted through the marked center of the hernia defect into the abdominal cavity, then the patch 106 is brought in contact with the needle edge, such that it touches the pre-marked point on the patch's surface. The patch can be elevated into its location while keeping the needle in the center point.
(d) Alternatively, the surgeon can use his/her finger in order to create a bulge in the center of the hernia, to which he/she can bring the center of the patch, while elevating it into contact with the patent's tissue.

What is claimed is:

1. A surgical instrument for closing an aperture in tissue, the surgical instrument comprising:
    a handle;
    a shaft connected to the handle, the shaft defining a longitudinal axis;
    a planar surgical mesh patch; and
    a deployment scaffold connected to a distal end of the shaft and configured for insertion into a cavity, wherein the deployment scaffold releasably retains the planar surgical mesh patch as the deployment scaffold transitions from an open configuration to a closed configuration back to the open configuration, the deployment scaffold being substantially X-shaped when in the open configuration, the deployment scaffold transitionable between the open and closed configurations in a plane extending along the longitudinal axis of the shaft, the deployment scaffold configured to tilt about the distal end of the shaft with respect to the longitudinal axis of the shaft.

2. The surgical instrument according to claim 1, wherein the deployment scaffold comprises:
    a plurality of deployment arms, each deployment arm of the plurality of deployment arms coupled to the shaft and to another deployment arm of the plurality of deployment arms at a central region of each deployment arm of the plurality of deployment arms; and
    a plurality of frame arms, each frame arm of the plurality of frame arms being movably coupled to a distal portion of each deployment arm of the plurality of deployment arms.

3. The surgical instrument according to claim 2, wherein the closed configuration is defined by the plurality of deployment arms being substantially parallel to each other.

4. The surgical instrument according to claim 2, wherein the open configuration is defined by one deployment arm of the plurality of deployment arms oriented at an angle between about 10° to about 180° with respect to another deployment arm of the plurality of deployment arms.

5. The surgical instrument according to claim 2, wherein each frame arm of the plurality of frame arms is configured to translate laterally between the open and closed configurations with respect to the longitudinal axis defined by the shaft.

6. The surgical instrument according to claim 1, wherein the shaft is reversibly transformable between a flexible configuration and a rigid configuration.

7. The surgical instrument according to claim 1, wherein the deployment scaffold is further configured for deployment of the planar surgical mesh patch and retraction of the planar surgical mesh patch while the deployment scaffold is deployed within the cavity.

8. The surgical instrument according to claim 1, wherein the deployment scaffold is usable in a plurality of deployment positions.

9. The surgical instrument according to claim 1, wherein the deployment scaffold includes an articulating member configured to adjust an orientation of the tilt of the deployment scaffold and the planar surgical mesh patch attached thereto with respect to the aperture in tissue.

10. The surgical instrument according to claim 9, wherein the articulating member is further configured to provide for vertical flexibility of the deployment scaffold in order to press the planar surgical mesh patch against the aperture in tissue and tilt the deployment scaffold.

11. The surgical instrument according to claim 1, wherein the the planar surgical mesh patch is connectable to the deployment scaffold with the deployment scaffold located exterior of the cavity.

12. The surgical instrument of claim 1, wherein the planar surgical mesh patch is a sheet of material.

13. A method for closing an aperture in tissue, the method comprising:

inserting a deployment scaffold in a closed configuration into a surgical site of a patient such that a portion of a shaft coupled to the deployment scaffold and a handle coupled to the shaft are positioned external of the surgical site, the shaft defining a longitudinal axis, the deployment scaffold tiltable about a distal end of the shaft with respect to the longitudinal axis;

deploying the deployment scaffold such that the deployment scaffold transitions in a plane extending along the longitudinal axis of the shaft from the closed configuration into a substantially X-shaped open configuration; and releasing a planar surgical mesh patch releasably retained on the deployment scaffold, the planar surgical mesh patch being releasably retained on the deployment scaffold as the deployment scaffold transitions from the open configuration to the closed configuration and back to the open configuration.

14. The method according to claim 13, wherein prior to releasing the planar surgical mesh patch the method further comprises adjusting the position and an orientation of the planar surgical mesh patch relative to the aperture in tissue.

15. The method according to claim 13, wherein releasing the planar surgical mesh patch from the deployment scaffold further includes releasing the planar surgical mesh patch relative to the aperture in tissue of an abdominal wall.

16. The method according to claim 13, wherein deploying the deployment scaffold and releasing the planar surgical mesh patch from the deployment scaffold further includes deploying the deployment scaffold and releasing the planar surgical mesh patch in a controlled and continuous manner.

17. The method according to claim 13, wherein prior to releasing the planar surgical mesh patch the method further comprises:

assessing the deployment of the planar surgical mesh patch relative to the aperture in tissue;

retracting the planar surgical mesh patch; and re-deploying the planar surgical mesh patch.

18. The method according to claim 13, wherein deploying the deployment scaffold includes:

deploying a plurality of deployment arms, each deployment arm of the plurality of deployment arms coupled to the shaft and to another deployment arm of the plurality of deployment arms at a central region of each deployment arm of the plurality of deployment arms; and deploying a plurality of frame arms, each frame arm of the plurality of frame arms being movably coupled to a distal portion of each deployment arm of the plurality of deployment arms.

19. The method according to claim 18, wherein inserting the deployment scaffold in the closed configuration further includes inserting the deployment scaffold such that the deployment arms are substantially parallel to each other.

20. The method according to claim 18, wherein deploying the deployment scaffold further includes orienting one deployment arm of the plurality of deployment arms at an angle between about 10° to about 180° with respect to another deployment arm of the plurality of deployment arms.

21. The method according to claim 13, further comprising transforming the shaft between a flexible configuration and a rigid configuration.

22. The method according to claim 13, wherein deploying the deployment scaffold into the open configuration further includes deploying the deployment scaffold into a deployment position of a plurality of deployment positions.

* * * * *